United States Patent [19]

Muschelknautz et al.

[11] 4,069,711
[45] Jan. 24, 1978

[54] METHOD AND APPARATUS FOR MEASURING THE GRAIN-SIZE OF FINE POWDERS

[75] Inventors: Edgar Muschelknautz, Leverkusen; Armin Bürkholz, Cologne; Wolfgang Richter, Opladen, all of Germany

[73] Assignee: Bayer Aktiengesellschaft, Leverkusen, Germany

[21] Appl. No.: 650,392

[22] Filed: Jan. 19, 1976

Related U.S. Application Data

[63] Continuation of Ser. No. 468,627, May 9, 1974, abandoned.

[30] Foreign Application Priority Data

May 15, 1973   Germany ............................. 2324421

[51] Int. Cl.² ..................... G01N 31/02, G01N 33/16
[52] U.S. Cl. ..................................................... 73/61.4
[58] Field of Search ........................................ 73/61.4, 73/61 R, 432 PS; 233/23 A

[56] References Cited

U.S. PATENT DOCUMENTS

| 3,074,627 | 1/1963 | Goetz ............................. 73/61.4 X |
| 3,206,983 | 9/1965 | Muschelknautz ..................... 73/61.4 |
| 3,679,367 | 7/1972 | Negersmith et al. ................. 73/61.4 |

FOREIGN PATENT DOCUMENTS

24,847   10/1969   Japan .................................... 73/61.4

Primary Examiner—Harry N. Haroian
Attorney, Agent, or Firm—Burgess, Dinklage & Sprung

[57] ABSTRACT

A method and an apparatus for measuring the grain-size of powders by measuring the changes in concentration of sedimentation liquids in a centrifugal field, wherein the displacement of two interconnected floats is measured in two separate sedimentation vessels.

15 Claims, 1 Drawing Figure

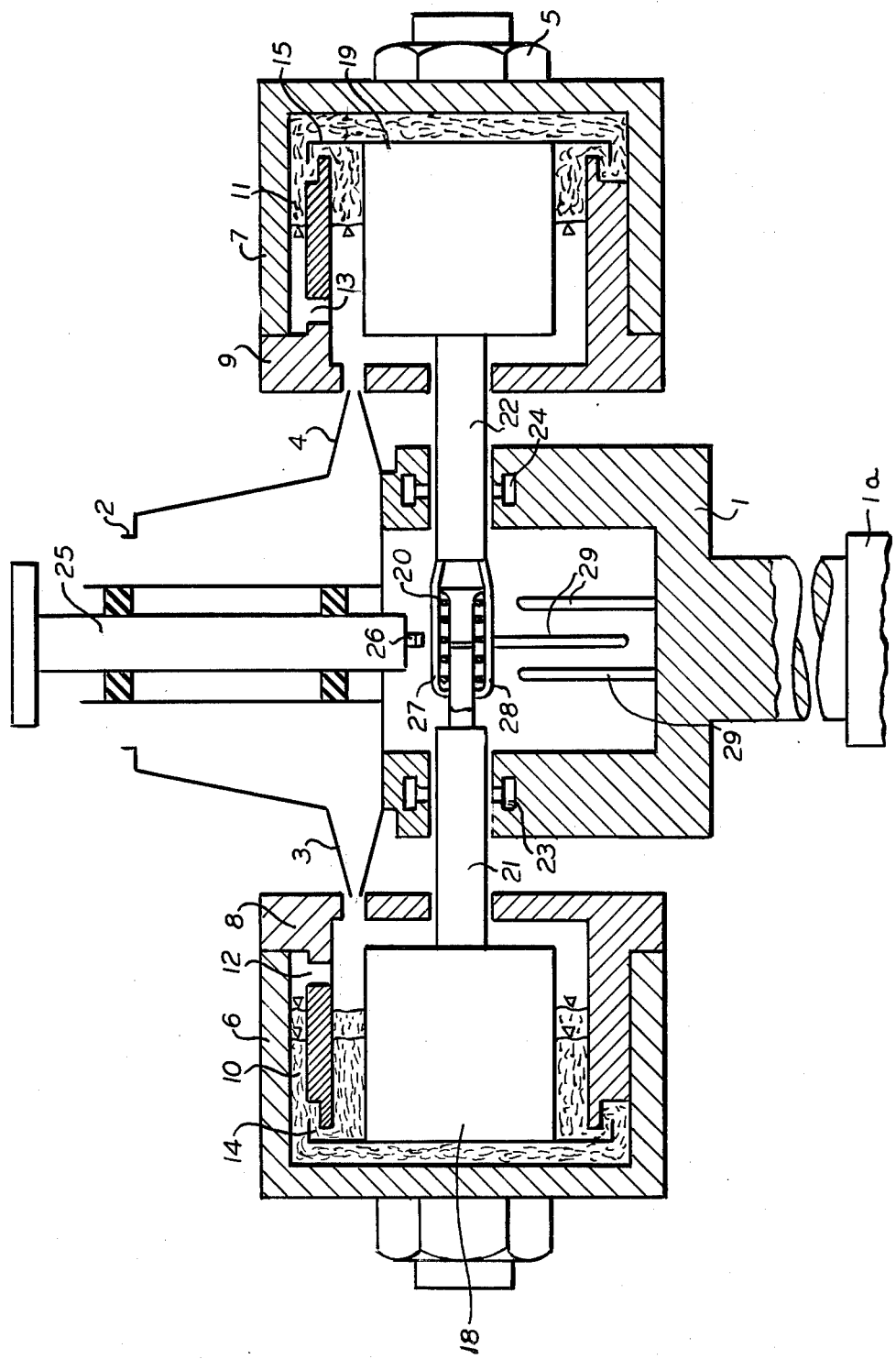

METHOD AND APPARATUS FOR MEASURING THE GRAIN-SIZE OF FINE POWDERS

This is a continuation of application Ser. No. 468,627, filed May 9, 1974.

This invention relates to a method for measuring the grain size of fine powders by measuring the changes in concentration of sedimentation liquids in a centrifugal field, and to apparatus for carrying out this method.

The method according to the invention, and the apparatus by which it is carried out, are intended to enable grain sizes of even fine powders having a wide grain size spectrum to be determined quickly and reliably.

There exist already various methods and apparatus for measuring grain size.

Grain size distribution can be calculated by measuring turbidity. Unfortunately, evaluation is extremely difficult and has been found by experience to lead to fairly considerable errors because the optical properties of the suspended particles are governed by the grain size itself.

In addition, there are systems in which small samples are taken during operation. Sampling during sedimentation is extremely difficult and, in most cases, interferes with the sedimentation process. Subsequent mass determination by evaporating the sedimentation liquid is time-consuming and inaccurate on account of the small quantities of fine powder.

There are also systems which measure the pressure difference of a suspension at different levels. Return pipes carry the liquid to a centre point and to the outside where a pressure gauge is situated. In systems of this kind, defective measurements are inevitable because it is not always possible for the return pipes to be completely vented.

In another known system, the increase in mass of the sediment in dependence upon the measuring time is followed by means of one or two settling plates. In this system, the centrifugal force of the sediment is measured by means of nozzle-baffle plate assemblies or by means of electrical force-measuring systems. On account of the measurement of force, rotational frequency or rpm should ideally remain constant. If it is desired to increase rotational frequency during sedimentation in order to shorten the process or, in the case of very wide grain-size distributions, to determine the ultra-fine fraction of the powder quickly and with the same degree of accuracy as the coarsest fractions, evaluation becomes extremely complicated and, in addition, inaccurate.

The object of the invention is to provide a method by which the sedimantation of suspended, preferably submicronic powders having a wide grain-size spectrum, can be measured quickly and with a high degree of accuracy.

According to the invention, there is provided a method for measuring the grain size of powders by measuring the changes in concentration of sedimentation liquids in a centrifugal field, wherein a displaceable measuring rod centered in the centrifugal field by coaxial arranged floats in liquid until said measuring rod, which is connected with coaxial settling plates in sedimentation vessels, is displaced by the difference of sedimentation rates of both opposite settling plates. The way (in time) is to be measured.

The advantages afforded by the method according to the invention are, in particular, the fact that the centrifugal force of the sediment and the lift of the floats are similarly proportional to the centrifugal acceleration. For this reason, an apparatus designed to carry out the method according to the invention can be operated at any rotational frequency.

In one embodiment of the method according to the invention, the rotational frequency is constant as a function of time.

With narrow grain-size distribution, it is possible in this way to measure grain size simply and reliably. This procedure is of particular advantage for routine investigations.

In another embodiment of the method according to the invention, the rotational frequency is varied in stages.

With a wide grain-size distribution, a measurement can be quickly obtained in this way.

In another embodiment of the method according to the invention, the rotational speed is steadily varied.

The particular advantage of this embodiment of the method according to the invention is that measurements can be taken very quickly, even with very wide grain-size distributions. In another embodiment of the method according to the invention, one sedimentation vessel is filled with sedimentation liquid and another is filled with pure liquid. In this way, it is possible to carry out measurements with low concentrations of fine powder.

The suspension is introduced into the sedimentation vessel while the rotor is running. To prevent the suspension surging into the sedimentation vessel from penetrating below the settling plate, which would inevitably give rise to faulty measurements, the sedimentation liquid is injected in with the settling plates locked in position this is another embodiment of the method according to the invention.

An apparatus for carrying out the method according to the invention comprises two diametrically opposed sedimentation vessels into each of which projects a float, and settling plates, all being joined together by displaceable connecting rods mounted in a mounting.

The advantages afforded by this embodiment of the arrangement according to the invention are, in particular, the fact that measurements can be carried out at a constant rotational frequency, at a rotational frequency variable in stages or at a steadily varied rotational frequency, because the position of the displaceable connecting rods is independent of the rotational frequency. By virtue of this arrangement, it is possible to shorten considerably the measuring times in the case of wide grain-size distributions. Another advantage of this embodiment is that minor fluctuations in rotational speed have no effect upon the result of measurement.

When the suspension to be measured is injected in, the settling plates are pressed against the input cylinders so that, at the beginning or measurement, the sedimentation liquid is situated in a precisely defined volume. In this way, inaccuracies are largely avoided. The stable equilibrium position of the measuring system as a whole is established through the floats connected to the settling plates which, through their lift, always compensate the weight of the system. The additional weight of the particular sediment settling on the plate is equalised by deeper immersion of the float. The resulting displacement of the system is measured and recorded on a recorder. Displacement of the system is preferably measured inductively, although it can also be measured by other methods, such as capacitive resistance measurement or pneumatic measurement. Since the degree of displacement during a single analysis amounts to around 200 μm, the sedimentation process is not disturbed. On the other hand, this displacement is sufficient for carrying out accurate measurement.

To prevent the forces which occur during measurement from being falsified, the bearings of the displaceable rods, in another embodiment of the apparatus according to the invention, are in the form of air bearings or magnetic bearings.

In another embodiment of the apparatus according to the invention, the sedimentation vessels are attached to tie rods.

To prevent air from coming into direct contact with the displaceable connecting rods during rotation, the connecting rods are arranged in the plane of rotation of the tie rods in another embodiment of the apparatus according to the invention.

In another embodiment of the apparatus according to the invention, the input cylinders are formed with pressure-equalising ducts and openings. The particular advantage of this is that, after on locking, the settling plates are also released from the input cylinders and are not held by any forces.

The measuring element used to measure the depth of penetration of the floats is with advantage fixed both to the connecting rods near the mounting in another embodiment of the apparatus according to the invention. By virtue of this arrangement of the measuring element in the vicinity of the axis of rotation, the forces acting on it are kept to a minimum.

In another embodiment of the arrangement according to the invention, a vertically displaceable rod 25 containing a pin 26 which holds two telescopic connecting rods, each with a stop between which a spring is arranged, in slots so that the settling plates are pressed against the input cylinders.

The particular advantage of this embodiment of the apparatus according to the invention is that the settling plates can be released during rotation. In addition, quick release of the settling plates makes it possible to measure coarse particles, thus considerably extending the measuring range of the apparatus according to the invention.

In another embodiment of the apparatus according to the invention, an injection vessel with radial, outwardly tapering outflow pipes, is arranged on the mounting.

In this way, suspensions can be injected or sprayed in while the centrifuge is in operation. Accordingly, disturbing start-up operations have no effect upon the result of measurement. The outwardly tapering outflow pipes provide for a very short injection time, and hence for thorough admixture with the pure sedimentation liquid in the vessel.

One embodiment of the apparatus according to the invention is described by way of example in the following with reference to the accompanying drawing, wherein:

FIG. 1 is a cross-section through an apparatus according to the invention.

Sedimentation vessels or input cylinders 6,7, mounted on tie rods 5, with input vessels 8,9 are arranged on a mounting or spindle 1, to which an injection vessel 2 having nozzles 3,4 is fixed, in such a way that they are diametrically opposed to each other. The input vessels 8,9 are provided with pressure-equalising ducts 10,11 and openings 12,13. The sedimentation vessels 6,7 are filled with sedimentation liquid in such a way that columns of sedimentation liquid differing in height are formed over settling plates 14,15 which are situated equal distances from axis. Floats 18,19 are arranged on the two settling plates 14,15, being joined together by means of two telescopic connecting rods 21,22 held by a compression spring 20. The connecting rods 21,22 together with the floats 18,19 and the settling plates 14,15 are moveable in air bearings 23,24. A vertically displaceable rod 25 with a pin 26 holds the connecting rods 21,22 in slots 27,28. The degree of displacement is measured by a displacement-measuring system 29 which is fixed to the rotatable mounting 1 and to the connecting rod 22. Means 1a is provided for driving the spindle 1 at a constant or varying r.p.m.

EXAMPLE

Measuring the Grain Size of Titanium Dioxide

For a specific density of 4 g/cc, the weight of sample amounted to 30 mg in 15 ml of water. After 10 minutes' ultrasonic treatment, and also after a 10 minute warm-up period for the measuring apparatus, the solids/water mixture was sprayed into the rotating measuring arrangement. At a rotational speed of 1620 r.p.m., analysis lasted 90 minutes. The grain size extended from 0.65 μm to 0.04 μm with an average at 0.26 μm. With a sedimentation path of 5 cm, sedimentation in the earth's gravitational field would have lasted approximately 17 days.

What we claim is:

1. In a centrifuge suitable for measuring particle size distribution of powder in a liquid dispersion, by sedimentation in the centrifugal field comprising:
   a. a rotatable spindle having a sedimentation vessel fixedly mounted thereon for rotation therewith for holding and centrifuging of a specimen of the dispersion,
   b. a settling plate disposed in the sedimentation vessel for receiving sediment of the powder, a connector for the settling plate, the settling plate being secured to the connector and the connector being mounted on the spindle for radial displacement of the settling plate in dependence on the centrifugal force acting on the settling plate due to accumulation of sediment thereon,
   c. gauge means for measuring said displacement as a measure of said particle size distribution,
   the improvement which comprises:
   d. buoyancy means attached to the connector for movement therewith for generating a force by buoyancy counteracting said centrifugal force and limiting said radial displacement of the connector so that the connector assumes a balanced position in dependence on the amount of sediment accumulated on the settling plate, said gauge means being for measuring the balance position.

2. Centrifuge of claim 1, said buoyancy means comprising a float attached to the connector for movement therewith.

3. Centrifuge of claim 2, the float being disposed for partial immersion in the dispersion in the sedimentation vessel.

4. Centrifuge of claim 1, and means for driving the spindle at constant r.p.m.

5. Centrifuge of claim 1, and means for driving the spindle at varying r.p.m.

6. Centrifuge of claim 1, the mounting of the connector on the spindle comprising an air bearing.

7. Centrifuge of claim 1, the mounting of the connector on the spindle comprising a magnetic bearing.

8. Centrifuge of claim 1, the sedimentation vessel having a pressure equalizing duct and an opening.

9. Centrifuge of claim 1, and an injection vessel mounted on the spindle and having a radial, outwardly tapering outflow pipe for introduction of the dispersion into the sedimentation vessel.

10. Centrifuge of claim 1, the connector being substantially centered on the spindle, said sedimentation vessel, settling plate, and buoyancy means being mounted on one end of the connector, and a second sedimentation vessel, settling plate and buoyancy means which are mounted in the same manner, on the other end of the connector.

11. Centrifuge of claim 10, the sedimentation vessels being mounted on the spindle by tie rods which are disposed at the same level as the connector.

12. Centrifuge of claim 10, wherein the connector comprises two aligned rods having their adjacent ends telescoped together, and spring means interposed between the rods and releasable lock means for releasably locking the settling plates with each settling plate pressing against the bottom of its sedimentation vessel.

13. Centrifuge of claim 10, each of the buoyance means comprising a float attached to the connector and disposed for partial immersion in dispersions centrifuged in the sedimentation vessels.

14. Centrifuge of claim 13, the mounting of the connector on the spindle comprising an air bearing.

15. Centrifuge of claim 13, the mounting of the connector on the spindle comprising a magnetic bearing.

* * * * *